United States Patent
Hackenberg

(10) Patent No.: US 6,266,998 B1
(45) Date of Patent: Jul. 31, 2001

(54) SYSTEM FOR MEASURING THE CONCENTRATION OF GASES

(75) Inventor: Michael Hackenberg, Lübeck (DE)

(73) Assignee: Drägerwerk Aktiengesellschaft (DE)

( * ) Notice: Subject to any disclaimer, the term of this patent is extended or adjusted under 35 U.S.C. 154(b) by 0 days.

(21) Appl. No.: 09/439,401

(22) Filed: Nov. 15, 1999

(30) Foreign Application Priority Data

Apr. 1, 1999 (DE) .............................................. 199 14 892

(51) Int. Cl.$^7$ .............................. G01J 1/50; G01N 21/78
(52) U.S. Cl. ........................ 73/31.05; 73/23.2; 422/83; 422/82.8; 422/57; 422/58; 422/88; 436/167
(58) Field of Search .................. 422/57, 58, 83, 422/63, 82.08, 86, 88, 93; 73/23.2, 31.05, 31.03; 436/167

(56) References Cited

U.S. PATENT DOCUMENTS

| | | | |
|---|---|---|---|
| 4,608,344 | * 8/1986 | Carter et al. | 436/34 |
| 4,872,759 | * 10/1989 | Stich-Baumeister et al. | 356/432 |
| 5,059,396 | * 10/1991 | Opitz et al. | 422/83 |
| 5,089,232 | * 2/1992 | May | 422/83 |
| 5,397,538 | * 3/1995 | Stark et al. | 422/83 |
| 5,415,838 | * 5/1995 | Rieger et al. | 422/57 |
| 5,464,588 | * 11/1995 | Bather et al. | 422/88 |
| 5,538,850 | * 7/1996 | King et al. | 422/57 |
| 5,998,221 | * 12/1999 | Malick et al. | 422/58 |
| 6,024,923 | * 2/2000 | Melendez et al. | 422/82.08 |
| 6,096,560 | * 8/2000 | Scripca et al. | 436/167 |

FOREIGN PATENT DOCUMENTS 39 02 402 C1   6/1990  (DE) .

OTHER PUBLICATIONS

Skoog, D.A. Principles of Instrumental Analysis, 1984, pp. 160–163.*

* cited by examiner

*Primary Examiner*—Hezron Williams
*Assistant Examiner*—Michael Cygan
(74) *Attorney, Agent, or Firm*—McGlew and Tuttle, P.C.

(57) ABSTRACT

A system for measuring the concentration of gases using gas-selective indicator substances in a chip-like carrier (1) with an optoelectronic scanning device (2). The chip-like carrier (2) has composite partial elements (3, 4) wherein one partial element (3) contains channels (5) for guiding the gas in the carrier (1), and another partial element (4) has at least one multireflection element (6) for guiding light. Each multireflection element (6) is provided with a layer (7) with indicator substances, which layer faces the gases to be measured and reacts with same in a gas-selective manner. The optoelectronic scanning device (2) has at least one radiation source (21) with an associated radiation detector (22), which are in optical functional connection with each multireflection element (6).

8 Claims, 2 Drawing Sheets

FIG. 2A
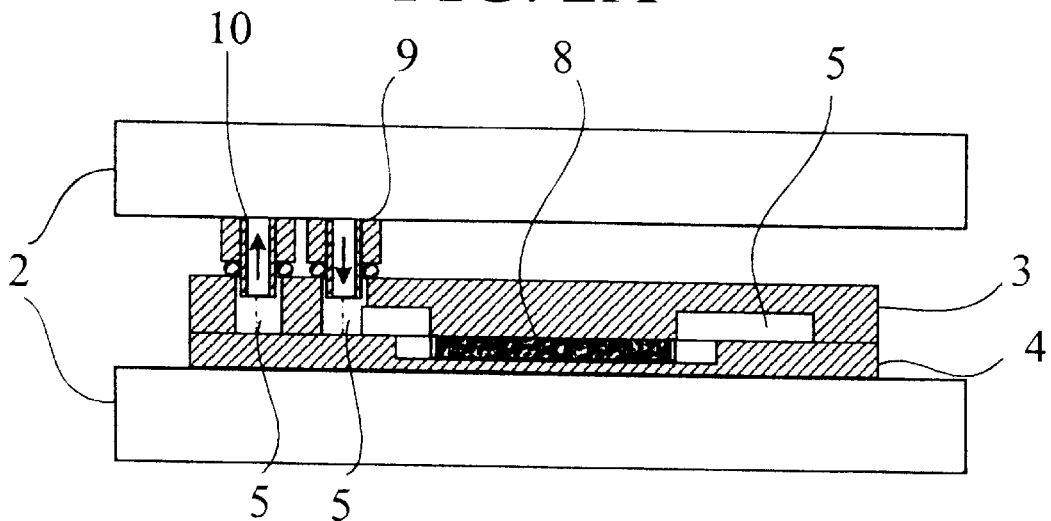
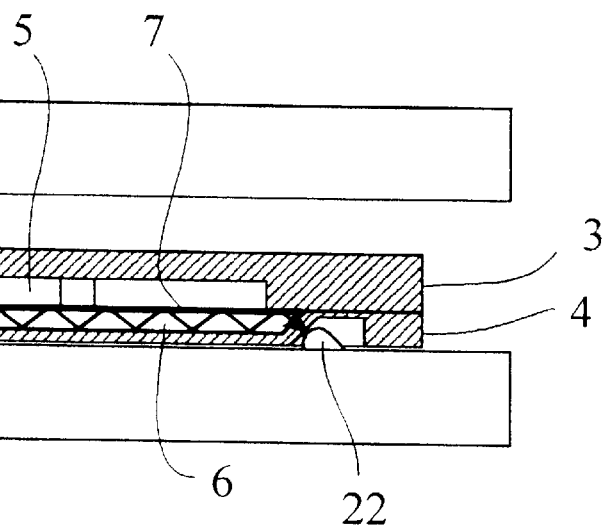
FIG. 2B

SYSTEM FOR MEASURING THE CONCENTRATION OF GASES

FIELD OF THE INVENTION

The present invention pertains to a system for measuring the concentration of gases using gas-selective, optically detectable indicator substances in a chip-like carrier wherein the change in the indicator substances is detected by means of an optoelectronic scanning device.

BACKGROUND OF THE INVENTION

Such a system has become known from DE 39 02 402 C1. One drawback of this prior-art arrangement is that the gas-sensitive indicator layer is scanned optically in a punctiform manner only, so that the measuring sensitivity is relatively low.

SUMMARY AND OBJECTS OF THE INVENTION

The object of the present invention is to provide a system of the type described in the introduction, which has increased measuring sensitivity and makes it possible to cover broader concentration ranges of the gases to be measured.

According to the invention, a system is provided for measuring the concentration of gases using gas-selective, optically detectable indicator substances in a chip-like carrier. The change in the indicator substances is detected by means of an optoelectronic scanning device. The chip-like carrier comprises a composite of partial elements wherein one partial element contains channels for guiding the gas in the carrier, and another partial element has at least one multireflection element for guiding light. Each multireflection element is provided with a layer with indicator substances, which layer faces the gases to be measured and reacts with same in a gas-selective manner. The optoelectronic scanning device has at least one radiation source with an associated radiation detector which are in optical functional connection with each multireflection element.

The essential advantage of the system according to the present invention is that despite its highly compact, material-saving design, it makes it possible to reach a substantially improved signal sensitivity and can be used in a versatile manner in terms of both different gases to be measured and different gas concentrations to be measured.

One essential component of the present invention is represented by the multireflection elements used with a layer containing optically detectable indicator substances, which layer faces the gases to be measured and reacts in a gas-selective and concentration-dependent manner. These multireflection elements are usually flat carriers made of optical materials, such as glass or a transparent plastic, which are provided with the said gas-sensitive layer on the top side. This layer is applied especially in the form of a solution or a dispersion, especially preferably as a colloid-disperse solution. Prior-art techniques for the application are especially spin coating, dip coating or inkjet metering. The function of the gas-sensitive layers is based on colorimetric reactions, i.e., the contact and the subsequent reaction with the gas to be measured lead to a change in color in the layer.

The degree of change in light transmission along the multireflection element is subsequently detected with a radiation detector by means of the light emitted by a radiation source, designed, e.g., as a diode (LED), the light being coupled in on one front side of the multireflection element at right angles to the oblique front surface. Based on multiple total reflection at the interfaces to the ambient air, the light coupled in passes through the gas-selective indicator layer a corresponding number of times. The light is again uncoupled on the opposite, likewise oblique front surface and is converted by a radiation detector, which is designed, e.g., as a photodiode, into an electric signal, which is subjected to further processing in an evaluating and calculating unit and is, in particular, displayed. Both the intensity of the change in the color of the gas-selective indicator layer and the time to a defined change in intensity may be used to evaluate the signals.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a top view and a phantom view of the chip-like carrier of the system according to the present invention and FIG. 2A is a sectional view of the carrier corresponding to the section lines IIA—IIA in FIG. 1, inserted into the optoelectronic scanning device in the measuring position; and FIG. 2B is a sectional view of the carrier corresponding to the section lines IIB—IIB in FIG. 1, inserted into the optoelectronic scanning device in the measuring position.

DESCRIPTION OF THE PREFERRED EMBODIMENTS

Figure 1:
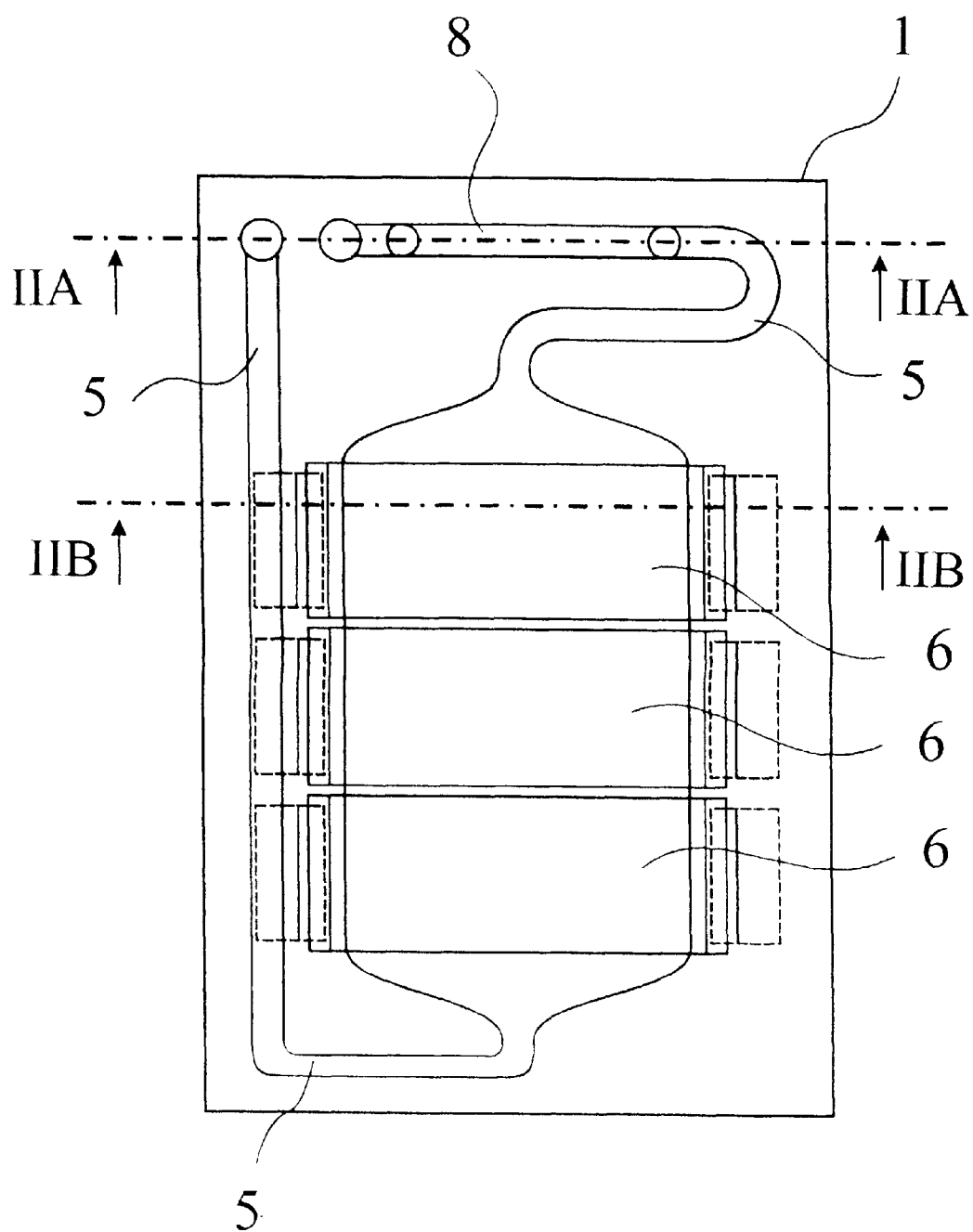

The chip-like carrier 1 according to FIG. 1 is preferably composed of two partial elements 3, 4, a bottom part and a top part. The partial element 3 designed as the top part comprises a preferably transparent plastic, especially one consisting of PMMA (polymethyl methacrylate), polycarbonate, polystyrene or polyacryl, and contains channels 5 for guiding gas through the carrier 1.

The partial element 4 designed as the bottom part (FIG. 2) consists of an optical plastic, preferably likewise PMMA, and has recesses on its top side for receiving the multireflection elements 6 made of glass or an optical plastic, and optionally for receiving gas-treating or gas-selectively prereacting reagents in the channel section 8. The recesses in the bottom part on the two outer front sides of the recesses with the multireflection elements 6 are used for adaptation to the optoelectronic scanning device 2 with at least one radiation source 21 each, especially in the form of a light-emitting diode (LED) and with an associated radiation detector 22, especially in the form of a photodiode. The beveled surfaces of the multireflection element 6 make it possible to couple the light in and out of the multireflection element 6, where it passes through the gas-selective layer 7 with total reflection and transmission. The top part of the optical scanning device 2 has a gas inlet 9 and a gas outlet 10 for connecting the carrier to an apparatus-side gas path for the gas to be measured, which is transported through the carrier 1 by means of a delivery element, not shown, especially a pump (the arrows in the upper part of FIG. 2 illustrate the pump induced gas flow).

In FIG. 1, the individual multireflection elements 6, specifically three elements in this particular case, are arranged at right angles to the direction of the flow of the gas to be measured through the carrier 1, so that the individual multireflection elements 6 are exposed to the entire gas flow of the measuring gas one after another.

Another possibility (not shown) of designing the carrier 1 and the optoelectronic scanning device 2 fitting it, is to design the channels 5 for guiding the gas (measuring gas channels) such that a separate gas path with separate gas treatment through a parallel channel section 8 is available for each multireflection element 6. As an alternative, a common, upstream channel section 8 may also be provided, depending on the application, in which case the gas path is divided into parallel gas paths with associated gas channels, comprising specific multireflection elements 6 and associated optoelectronic scanning devices 2. The latter possibility of embodiment is particularly suitable for applications in which the gas treatment is the same for all measuring gas channels and measuring elements, e.g., for drying the measuring gas, but separate measuring gas channels are needed, because a measuring gas mixture consisting of different gases is to be measured, so that each parallel measuring gas channel will be measured separately.

The evaluation by means of the optoelectronic scanning device 2 takes place, in general, such that the radiation sources 21 emit modulated light and the light emitted from the multireflection element 6 is received in the radiation detectors 22 and is converted into electric signals.

The signal processing is preferably performed in an evaluating and calculating unit, not shown, by means of suitable amplifiers, filter and calculating elements, so that the concentration-dependent change in the gas-selective layer 7 of one or more multireflection elements 6, which change is caused by a gas to be detected, and the associated, concentration-dependent change in the light signals received by means of the radiation detectors 22, are used to determine the concentration of the gas to be measured.

The design of the carrier 1 according to FIGS. 1 and 2 shown make possible the use of multireflection elements 6 with layers 7 containing indicator substances of the same type at different concentrations, and thus it offers the possibility of expanding the dynamic range of measurement. If the measuring sensitivity of the individual multireflection elements 6 is selected to be such that the measuring sensitivities of the elements will overlap, an improvement in the measuring accuracy, i.e., a reduction of the standard deviation, can be achieved by taking into account the redundant signals, in addition to the expansion of the measuring range.

In the embodiment according to FIGS. 1 and 2, the multireflection element 6 with the lowest concentration, i.e., with the highest sensitivity, should be the first element in the gas path, and this element 6 will thus be the first element to send corresponding measured signals. The coating of the multireflection elements 6 with gas-selectively reacting indicator substances in layers 7 may be applied in all forms known to the person skilled in the art, especially in the form of solutions, dispersions, as colloid-disperse solutions, or even in the form of films or in combined application forms, e.g., by means of the especially preferred sol-gel process.

Two examples for coating the multireflection elements 6 for measuring NO and $NO_2$ in a gas mixture or $No_2$ alone will be described below:

1. Simultaneous Detection of $NO/NO_2$
1.1. Coating of the Multireflection Elements 6

A according to a process called the sol-gel process for colloid-disperse solutions for coating the multireflection elements 6 is suitable for the simultaneous detection of $NO/NO_2$. The coating solution consists of two components. The first component is a sol-gel precondensate for producing silica gel as a carrier substance. The other component is the detection-specific indicator solution, which is an o-tolidine solution in this case and which generates a change in color from colorless to green upon the entry of $NO_2$.

Precondensate

Charge 20 mL of tetramethoxysilane and 20 mL of ethanol into a glass vessel and stir into ice water with a magnetic stirrer, add 10 mL of 0.01-m HCl and stir for about 5 minutes. The precondensate is subjected to further processes only 24 hours later.

$NO_2$ indicator solution (o-tolidine solution)

Mix 0.425 g of o-tolidine and 93 mL of ethylene glycol with a magnetic stirrer.

Coating Solution

Mix 10 mL of $NO_2$ indicator solution and 10 mL of precondensate with a magnetic stirrer.

The layer is applied by means of the spin coating process. One hundred $\mu L$ of coating solution are applied for this centrally to a multireflection element 6 and centrifuged at 3,000 revolutions per minute. The result is a very thin, homogeneous and reproducible $NO_2$-sensitive layer.

To make it possible to also detect the concentration of NO besides the concentration of $NO_2$, two different gas treatments are necessary. A carrier 1 with two parallel, separate channels 5 and with an associated pretreatment in separate, upstream channel sections 8 is therefore needed for this application.

1.2. Chemicals for Pretreating the Gas

A gas-pretreatment layer, which makes it possible to stabilize the moisture content, on the one hand, and oxidies NO into $NO_2$, on the other hand, is introduced into a channel section 8. Consequently, both NO and $NO_2$ are detected with the downstream multireflection element 6.

A gas-pretreatment layer, which is used only to stabilize the moisture content, is introduced into the other channel section 8. The multireflection element 6 arranged downstream here consequently detects $NO_2$ only. The concentration of NO can be determined by forming the difference between the two signals.

2. Detection of NO, with Improved Measurement Dynamics and Accuracy

A measuring device according to FIGS. 1 and 2 is used for this application; this measuring device has, e.g., three multireflection elements 6, which are located in series and at right angles to the gas flow. The multireflection elements 6 are provided with $NO_2$-sensitive layers 7 of different sensitivities. The coating solutions for this are obtained by varying the mixing ratios of the precondensate and o-tolidine solutions.

Coating Solution 1

Mix 20 mL of $NO_2$ indicator solution and 10 mL of precondensate with a magnetic stirrer.

Coating Solution 2

Mix 10 mL of $NO_2$ indicator solution and 10 mL of precondensate with a magnetic stirrer.

Coating Solution 3

Mix 10 mL of $NO_2$ indicator solution and 20 mL of precondensate with a magnetic stirrer.

The three multireflection elements 6 are coated according to the spin coating process as in the above example.

The multireflection element 6 with the most sensitive indicator layer is positioned in the carrier 1 such that when gas is admitted, it is the first to be exposed to the gas to be tested. In the case of a very low $NO_2$ concentration, it generates a usable measured signal. If the $NO_2$ concentration is too high, its color changes immediately, and the next, more insensitive multireflection elements 6 can determine the concentration. A very broad concentration range of $NO_2$ is thus covered.

Since the sensitivity of the multireflection element 6 is selected here to be such that two multireflection elements 6 always send a valuable signal simultaneously, this redundancy also improves the measuring accuracy by corresponding calculations.

Using the system according to the present invention, it is possible to measure gas concentrations at high sensitivity, which makes it possible to reduce the concentration detection limits, on the one hand, and to reduce the measuring time, on the other hand.

Measuring gas channels with highly defined and low flow resistances are obtained, as a result of which the parallel admission of a gas to a plurality of multireflection elements 6 is also possible.

The application of the gas-specific and gas-selective layers 7 is simple and inexpensive. In addition, the layers 7 with the indicator substances can be applied homogeneously and reproducibly according to printing and application techniques, such as ink jet metering, spin coating, dip coating, which is advantageous for the measuring accuracy.

While specific embodiments of the invention have been shown and described in detail to illustrate the application of the principles of the invention, it will be understood that the invention may be embodied otherwise without departing from such principles.

What is claimed is:

1. A gas concentration measuring arrangement, comprising:

a carrier including composite partial elements defining a channel for guiding the gas in the carrier;

a multireflection element for guiding light including a first end, a second end, a first surface and an opposite second reflection surface, said multireflection element being supported in said carrier, said carrier including a multireflection element receiving space, said multireflection element being disposed in said multireflection element receiving space;

an indicator substance layer provided on said first surface of said multireflection element, said multireflection element being disposed in said multireflection element receiving space with said layer being positioned in said channel for guiding the gas in the carrier, said layer defining a delimiting surface of said channel for contact with the gases to be measured, said indicator substance being a predefined substance for reaction with a predefined gas or gas mixture, said reaction including an indicator color change;

an optoelectronic scanning device connected to said carrier, said optoelectronic scanning device sensing a degree of light transmission along said multireflection element said optoelectronic scanning device detecting one of an intensity of a change in color of said indicator and a time until a defined change in intensity of a change in color of said indicator, said optoelectronic scanning device having a radiation source coupled to said first end directed toward said multireflection element to reflect off said first surface and said reflection surface multiple times as the radiation travels from said first end to said second end and with an associated radiation detector coupled to said second end and in optical functional connection with said multireflection element, another multireflection element for guiding light, said another multireflection element having a first end, a second end, a first surface and an opposite second reflection surface, said another multireflection element being supported in said carrier, said carrier including another multireflection element receiving space, said another multireflection element being disposed in said another multireflection element receiving space;

another indicator substance layer provided on said first surface of said another multireflection element, said another multireflection element being disposed in said second multireflection element receiving space with said another layer being positioned in said channel for guiding the gas in the carrier, said another layer defining a delimiting surface of said channel for contact with the gases to be measured, said another indicator substance being a predefined substance for reaction with a predefined gas or gas mixture, said reaction including an indicator color change, said another indicator substance being different from said indicator substance qualitatively in a substance dependent manner and/or quantitatively in a concentration-dependent manner; and another optoelectronic scanning device connected to said carrier, said another optoelectronic scanning device sensing a degree of light transmission along said another multireflection element, said another optoelectronic scanning device detecting one of an intensity of a change in color of said another indicator substance and a time until a defined change in intensity of a change in color of said another indicator substance, said another optoelectronic scanning device having a radiation source coupled to said first end of said another multireflection element directed towards said another multireflection element to reflect off said first surface of said another multireflection element and said reflection surface of said another multireflection element multiple times as the radiation travels from said first end of said another multireflection element to said second end of said another multireflection element and with an associated radiation detector coupled to said second end of said another multireflection element and in optical functional connection with said another multireflection element.

2. The arrangement in accordance with claim 1, further comprising; a gas-treatment or gas-selectively prereacting material, wherein said channel section is provided in said carrier with said gas-treatment or gas-selectively prereacting material, which is permeable for the gas flowing through in front of a first multireflection element or of each said multireflection element in a direction of gas flow.

3. The arrangement in accordance with claim 1, wherein said optoelectronic scanning device transmits light as the radiation and said multireflection element is arranged trans mitting the light essentially at right angles to a direction of gas flow or essentially in parallel to a direction of gas flow.

4. The arrangement in accordance with claim 1, further comprising closing elements wherein said carrier is provided with said closing elements for said channel, which are removed or perforated before measurement.

5. The arrangement in accordance with claim 1, wherein said multireflection element is provided with an optical carrier material of glass or an optical plastic, and said gas-selectively reacting layer is applied in the form of one of a film, a solution, a dispersion or a colloid-disperse solution.

6. The arrangement in accordance with claim 1, wherein said partial elements of said carrier are formed of transparent plastic using an injection molding process.

7. The arrangement in accordance with claim 1, wherein said carrier is provided with a gas-tight envelope.

8. The arrangement in accordance with claim 7, wherein said gas-tight envelope includes a metal or a metal/plastic film, which is removed before measurement.

* * * * *